United States Patent [19]

Ainsworth et al.

[11] 4,385,066
[45] May 24, 1983

[54] ARYLETHANOLAMINE DERIVATIVES, THEIR PREPARATION AND USE IN PHARMACEUTICAL COMPOSITIONS

[75] Inventors: Anthony T. Ainsworth, Cranleigh; David G. Smith, Redhill, both of England

[73] Assignee: Beecham Group Limited, England

[21] Appl. No.: 263,168

[22] Filed: May 13, 1981

[30] Foreign Application Priority Data

May 22, 1980 [GB] United Kingdom ............... 8016890

[51] Int. Cl.$^3$ .................... A61K 31/24; C07C 101/30
[52] U.S. Cl. .................................. 424/309; 560/42; 562/451; 564/165; 424/319; 424/324
[58] Field of Search ............. 560/42; 562/451; 564/165; 424/309, 319, 324

[56] References Cited

U.S. PATENT DOCUMENTS

| | | | |
|---|---|---|---|
| 3,723,524 | 3/1973 | Augstein et al. | 564/165 |
| 3,911,008 | 10/1975 | Edinberry et al. | 564/165 |
| 4,086,272 | 4/1978 | Cox et al. | 260/501.17 |
| 4,140,713 | 2/1979 | Oxford et al. | 564/165 |

FOREIGN PATENT DOCUMENTS 6735 1/1980 European Pat. Off. .
6766 1/1980 European Pat. Off. .

Primary Examiner—Bernard Helfin
Attorney, Agent, or Firm—Jacobs & Jacobs

[57] ABSTRACT

Compounds of formula (II):

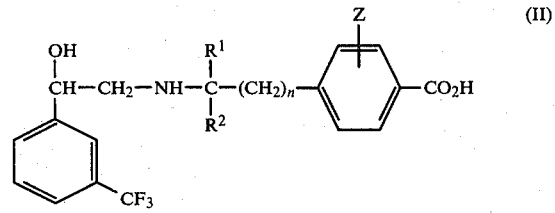

or a pharmaceutically acceptable salt, lower alkyl or aralkyl ester or amide thereof, wherein $R^1$ and $R^2$, which may be the same or different, are each of a hydrogen atom or a methyl group, n is 1, 2 or 3, and Z is a $C_{1-6}$ alkyl or $C_{1-6}$ alkoxy group, or a halogen or hydrogen atom are useful in treating obesity and/or hyperglycaemia and/or inflammation in mammals.

12 Claims, No Drawings

ARYLETHANOLAMINE DERIVATIVES, THEIR PREPARATION AND USE IN PHARMACEUTICAL COMPOSITIONS

The present invention relates to a group of arylethanolamine derivatives which have anti-obesity and/or hypoglycaemic activity, to processes for their preparation and to their use in medicine.

European Patent Application No. 79 301197.4 discloses compounds of formula (I):

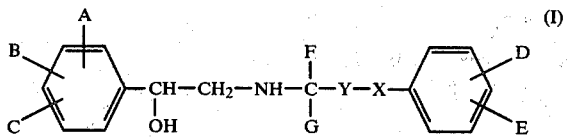

wherein
A is hydrogen, fluorine, chlorine, hydroxyl, hydroxymethyl, methyl, methoxy, amino, formamido, acetamido, methylsulphonamido, nitro, benzyloxy, methylsulphonylmethyl, ureido, trifluoromethyl or p-methoxybenzylamino;
B is hydrogen, fluorine, chlorine or hydroxyl;
C is hydrogen, fluorine, chlorine or hydroxyl;
D is a carboxylic acid group or a salt, ester or amide thereof;
E is hydrogen, fluorine, chlorine, methyl, methoxy, hydroxyl or a carboxylic acid group or a salt, ester or amide thereof;
F is hydrogen, methyl, ethyl or propyl;
G is hydrogen, methyl, ethyl or propyl;
X is oxygen or a bond; and
Y is $C_{1-6}$ alkylene or a bond,
which possess anti-obesity and/or hypoglycaemic activity.

We have now discovered a group of compounds somewhat related to those of the above European Patent Application which have unusually potent anti-obesity and/or hypoglycaemic activity, coupled with low cardiac stimulant activity. Compounds of this invention also have topical anti-inflammatory activity.

According to the present invention there is provided a compound of formula (II):

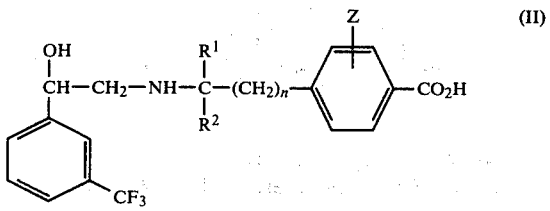

or a pharmaceutically acceptable salt, lower alkyl or aralkyl ester or amide thereof, wherein $R^1$ and $R^2$, which may be the same or different, are each a hydrogen atom or a methyl group, n is 1, 2 or 3, and Z is a $C_{1-6}$ alkyl or $C_{1-6}$ alkoxy group, or a halogen or hydrogen atom.

Preferably $R^1$ is a hydrogen atom and $R^2$ is a methyl group.

Preferably n is 1 or 2, most preferably 1.

Preferred esters are the methyl, ethyl, propyl and benzyl esters. In the case of an amide, the amide group may be substituted by one or two $C_1$ to $C_4$ alkyl groups, preferably methyl groups, or it may be unsubstituted.

Suitably Z is a methyl, ethyl, methoxy or ethoxy group, or is a chlorine or hydrogen atom.

Particularly suitable compounds of this invention include those of formula (III):

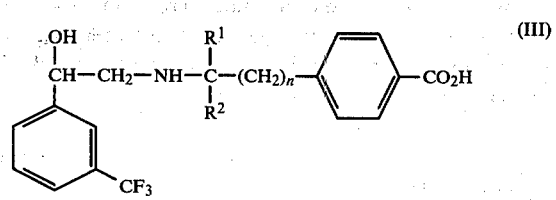

or a pharmaceutically acceptable salt, lower alkyl or aralkyl ester or amide thereof, wherein $R^1$ and $R^2$, which may be the same or different, are each a hydrogen atom or a methyl group and n is 1, 2 or 3.

The compounds of this invention may be provided as acid addition salts. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salycyclic or acetylsalycyclic acid.

The compounds of formula (II) have a centre of asymmetry at the carbon atom marked with a single asterisk in formula (IIa):

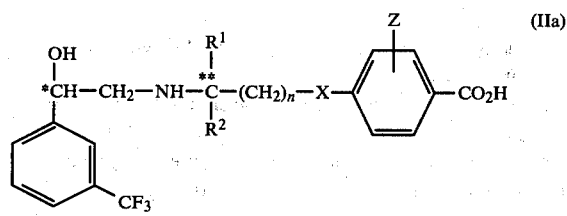

in which $R^1$, $R^2$, Z and n are as defined in relation to formula (II). The compounds have another centre of asymmetry at the carbon atom marked with two asterisks in formula (IIa) when $R^1$ is different from $R^2$.

The compounds may, therefore, exist in at least two and often four stereoisomeric forms. The present invention encompasses all stereoisomers of the compounds of formula (II) whether free from other stereoisomers or admixed with other stereoisomers in any proportion and thus includes, for instance, racemic mixtures of enantiomers.

Preferably both the *C and **C atoms have the R absolute stereochemical configuration, or the *C atom has the R configuration and the **C atom has the S configuration.

The absolute configuration of any compound of formula (II) may be determined by conventional X-ray cystallographic techniques.

It is believed that, in the $^{13}C$ n.m.r. of compounds of formula (II) wherein one of $R^1$ and $R^2$ is hydrogen and the other is methyl, the diastereoisomer having the greater anti-obesity activity is that for which the signal of the methyl group carbon atom appears at higher field (the lower numerical value when expressed in ppm) in $d_6$DMSO solution. The paired resonances often appear at approximately 20 ppm (less active) and slightly below 20 ppm (more active) down field from tetramethylsilane. Other paired resonances can occur for the carbon atoms attached directly to the nitrogen atom and the carbon which carries the hydroxyl and phenyl groups. Again the paired resonances of the more active diastereoisomer of the investigated compounds appear at the higher field position.

The present invention also provides a process for producing a compound of formula (II) or a salt, ester or amide thereof, which process comprises reducing an oxo-group and/or a double bond of a compound of formula (IV):

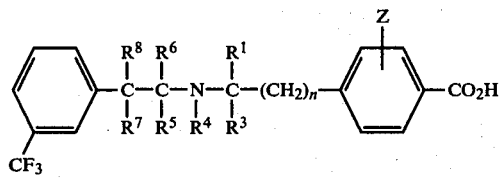
(IV)

or a pharmaceutically acceptable salt, ester or amide thereof, wherein $R^1$, Z and n are as defined in relation to formula (II).

$R^3$ is a group $R^2$ as defined in relation to formula (II) or together with $R^4$ forms a bond;

$R^4$ is hydrogen or together with $R^3$ or $R^5$ forms a bond;

$R^5$ is hydrogen or together with $R^6$ forms an oxo-group or together with $R^4$ forms a bond;

$R^6$ is hydrogen or together with $R^5$ forms an oxo-group;

$R^7$ is hydrogen or hydroxyl or together with $R^8$ forms an oxo-group;

$R^8$ is hydrogen or together with $R^7$ forms an oxo-group, provided that there is no more than one oxo-group and no more than one bond represented by any of $R^3$ to $R^8$.

The aforementioned reductions may be effected by conventional chemical or catalytic methods, such as chemical reduction using diborane sodium cyanoborohydride or sodium borohydride or by catalytic hydrogenation using catalysts such as palladium on charcoal, or platinum, for instance, as platinum oxide.

Reduction by sodium borohydride is conveniently effected in a lower alkanolic solvent such as methanol. The reaction is generally carried out at from 0°–20° C.

Catalytic reduction is conveniently effected in a conventional hydrogenation solvent such as a lower alkanol, for instance ethanol. The hydrogenation is generally carried out under hydrogen gas at about 1 atmosphere pressure to about 10 atmospheres pressure and at ambient or elevated temperature.

In particular process aspects, the present invention provides processes for producing compounds of formula (II) by reducing a compound of formula (IVA):

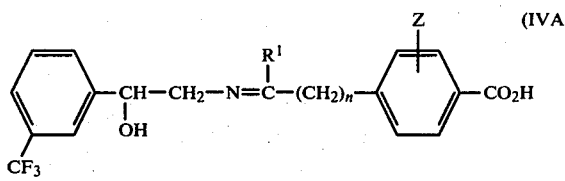
(IVA)

or reducing a compound of formula (IVB):

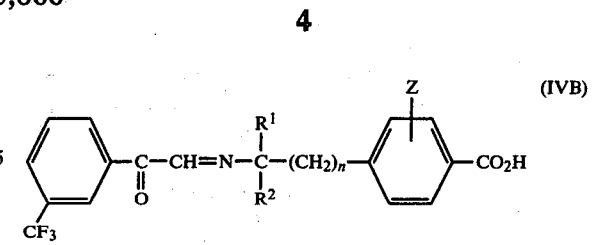
(IVB)

or reducing a compound of formula (IVC):

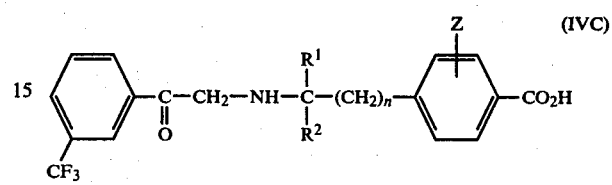
(IVC)

or reducing a compound of formula (IVD):

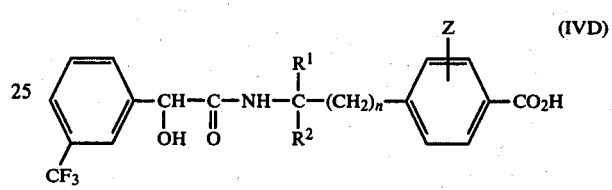
(IVD)

or their pharmaceutically acceptable salts, esters or amides wherein $R^1$, $R^2$, Z and n are as defined in relation to formula (II).

The present invention also provides another process for producing a compound of formula (II) or a salt, ester or amide thereof, which process comprises reacting a compound of formula (V):

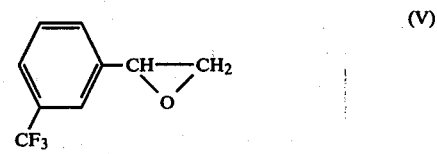
(V)

with a compound of formula (VI):

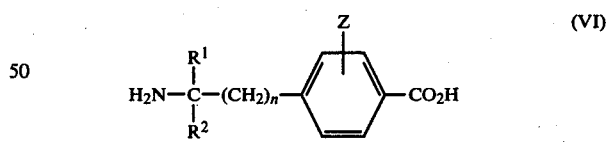
(VI)

or a salt, ester or amide thereof,
wherein $R^1$, $R^2$, Z and n are as defined in relation to formula (II).

This reaction is conveniently effected in a solvent such as a lower alkanol, preferably ethanol.

A particularly preferred process for producing compounds of formula (II) comprises the reduction of a compound of formula (IVA), especially using sodium borohydride in methanol at ambient temperature.

The salts of compounds of formula (II) may be produced by treating the compound of formula (II) with the appropriate acid.

Compounds of formula (II), produced by the above processes, may be recovered by conventional methods.

Compounds of formula (II) having a single asymmetric carbon atom may, if desired, be separated into individual enantiomers by conventional means, for example, by the use of an optically active acid as a resolving agent. Those compounds of formula (II) having two asymmetric carbon atoms may be separated into diastereoisomeric pairs of enantiomers by, for example, fractional crystallisation from a suitable solvent such as ethyl acetate. The pair of enantiomers thus obtained may be separated into individual stereoisomers by conventional means such as by the use of an optically active acid as a resolving agent.

Suitable optically active acids which may be used as resolving agents are described in "Topics in Stereochemistry" Vol 6, Wiley Interscience, 1971, Allinger, N. L. and Eliel, W. L. Eds.

Alernatively any enantiomer of a compound of formula (II) may be obtained by stereospecific synthesis using an optically pure starting material of known configuration.

Compounds of formula (IV) may be produced by reacting a compound of formula (VII):

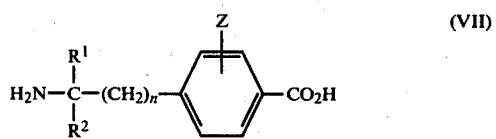

(VII)

or a pharmaceutically acceptable salt, ester or amide thereof, wherein $R^1$, $R^2$, Z and n are as defined in relation to formula (II),
with a compound of formula (VIII):

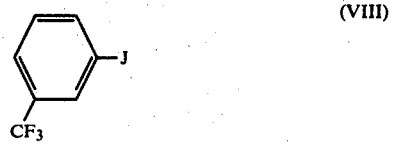

(VIII)

wherein
J is a reactive moiety which is capable of reacting with the amine of formula (VII) thus forming a compound of formula (IV). Typical examples of compounds of formula (VIII) are:

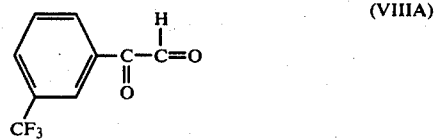

(VIIIA)

or its hydrate or hemi-acetal of a lower alkanol;

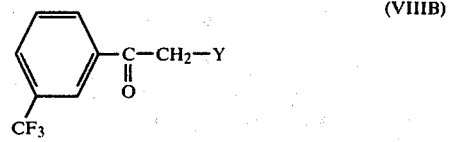

(VIIIB)

wherein Y is a halogen atom, preferably bromine

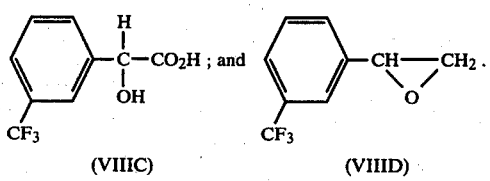

Conventional conditions suitable for use with the particular compound of formula (VIII) may be used for this reaction. Thus the reaction of a compound of formula (VIIIA) with a compound of formula (VII) is conveniently conducted at elevated temperature under conditions resulting in the removal of the water formed during the reaction. A particularly suitable method is to perform the reaction in a solvent, such as benzene, under reflux and azeotropically to remove the water using a Dean & Stark trap.

The reaction of a compound of formula (VIIIB) with a compound of formula (VII) is conveniently conducted in a polar organic solvent such as acetonitrile or butanone, at an elevated temperature, for instance under reflux.

The reaction of a compound of formula (VIIIC) with a compound of formula (VII) is conveniently conducted under standard peptide formation reaction conditions.

The reaction of a compound of formula (VIIID) with a compound of formula (VII) is conveniently conducted in a solvent such as a lower alkanol, preferably ethanol.

By using single enantiomers of a compound of formula (VII) and a compound of formula (VIII) such as the compounds (VIIIC) or (VIIID) a stereospecific synthesis of a compound of formula (IV) is achieved. This may then be reduced to a compound of formula (II) without altering the configuration of the two asymmetric carbon atoms. Thus, for example, a compound of formula (VII) with the R absolute configuration and a compound of formula (VIIID) with the R absolute configuration would afford a compound of formula (II) with the RR absolute configuration.

Certain compounds of formula (IV) may also be produced by reacting a compound of formula (IX):

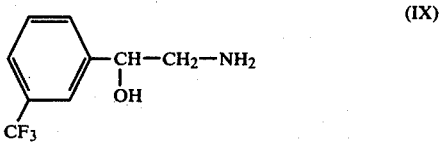

(IX)

with a compound of the formula (X):

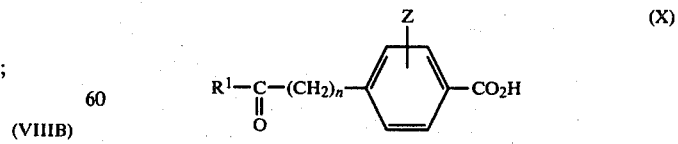

(X)

or a pharmaceutically acceptable salt, ester or amide thereof, wherein $R^1$, Z and n are as defined in relation to formula (II).

This reaction is conveniently effected under conditions which result in the removal of water formed during the reaction. A particularly suitable method is to perform the reaction in a solvent, such as benzene, under reflux and azeotropically to remove the water using a Dean & Stark trap.

It is often convenient to prepare the compound of formula (IV) and reduce it, in situ, to the desired compound of formula (II) without isolation of the compound of formula (IV).

A compound of formula (II) or a pharmaceutically acceptable salt, ester or amide thereof (hereinafter "the drug") may be administered as the pure drug, however, it is preferred that the drug be administered as a pharmaceutical composition also comprising a pharmaceutically acceptable carrier.

Accordingly, the present invention also provides a pharmaceutical composition comprising a compound of the formula (II) or a pharmaceutically acceptable salt, ester or amide thereof, with a pharmaceutically acceptable carrier therefor.

As used herein the terms "pharmaceutical composition" and "pharmaceutically acceptable" embrace compositions and ingredients for both human and veterinary use.

Usually the compositions of the present invention will be adapted for oral administration although compositions for administration by other routes, such as by injection, are also envisaged.

Particularly suitable compositions for oral administration are unit dosage forms, such as tablets and capsules. Other fixed-unit dosage forms, such as powders presented in sachets, may also be used.

In accordance with conventional pharmaceutical practice the carrier may comprise a diluent, binder, filler, disintegrant, wetting agent, lubricant, colourant, flavourant, or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 500 mg of the drug, more usually 0.1 to 250 mg and favourably 0.1 to 100 mg.

The present invention further provides a method for treating obesity in human or non-human animals, which method comprises administering an effective, non-toxic amount of a compound of formula (II) or a pharmaceutically acceptable salt, ester or amide thereof to obese human or non-human animals.

In treating obese humans, the drug may be taken in doses, such as those described above, one to six times a day in a manner such that the total daily dose for a 70 kg adult will generally be about 0.1 to 1000 mg, and more usually about 1 to 500 mg.

In treating obese non-human animals, especially dogs, the drug may be administered by mouth, usually once or twice a day and at about 0.025 mg/kg to 2.5 mg/kg, for example 0.1 mg/kg to 2 mg/kg.

The present invention further provides a method for treating hyperglycaemia in humans which method comprises administering an effective, non-toxic amount of a compound of formula (II) or a pharmaceutically acceptable salt, ester or amide thereof, to hyperglycaemic humans.

The drug may be taken in doses such as those described above for treating obese humans.

The present invention further provides a method for treating inflammation in human and non-human animals, which method comprises administering an effective, non-toxic amount of a compound of formula (II) or a pharmaceutically acceptable salt, ester or amide thereof, to the animal.

The invention will now be illustrated with reference to the following Examples, which are not intended to limit the scope in any way.

EXAMPLE 1

N-(2-(4-Carbomethoxyphenyl)-1-methylethyl)-2-hydroxy-2-(3-trifluoromethylphenyl) ethanamine (a) A mixture of 3-trifluoromethylphenyl glyoxal (2.1 g) and 2-(4-carbomethoxyphenyl)-1-methylethanamine (2.0 g) in benzene (150 ml) was refluxed under Dean & Stark conditions for 2 hours. The solvent was replaced with methanol (150 ml), the mixture was cooled in ice and sodium borohydride (4.0 g) was added portionwise. The mixture was stirred at ambient temperature for 3 hours, the solvent was evaporated and the residue was partitioned between water (100 ml) and chloroform (100 ml). The aqueous phase was further extracted with chloroform (100 ml), the combined organic extracts were dried (Mg SO$_4$) and evaporated to an oil which was crystallised from hexane to give the title compound, m.p. 80°–83° as a 25:75 mixture of diastereoisomers. (25% RR,SS:75% RS,SR). $\tau$(CDCl$_3$) 8.95 (3H,d,J=6 Hz) 6.6–7.6 (5H,m), 6.13 (3H,s), 5.3 (1H,m) 2.72 (2H,d,J=8 Hz), 2.1–2.5 (4H,m), 1.92 (2H,d,J=8 Hz).

(b) A mixture of 1-(4-carbomethoxyphenyl)propan-2-one (2.25 g) and 2-hydroxy-2-(3-trifluoromethylphenyl)ethanamine (2.4 g) in benzene (100 ml) was refluxed under Dean & Stark conditions for 2 hours. The resulting adduct was reduced with sodium borohydride and the product was isolated as in part 1). Crystallisation from ether gave the title compound m.p. 73°–88° as a 50:50 mixture of diastereoisomers. Recrystallisation of this mixture from ethyl acetate gave a sample m.p. 82°–85°, predominantly the RS,SR diastereoisomer (12:88).

EXAMPLE 2

N-(3-(4-Carbomethoxyphenyl)-1-methylpropyl)-2-hydroxy-2-(3-trifluoromethylphenyl)ethanamine A solution of 2-hydroxy-2-(3-trifluoromethylphenyl) ethanamine (3 g) and 4-(4-carbomethoxyphenyl)butan-2-one (3 g) in benzene was boiled for 2½ hours with azeotropic removal of water and then evaporated to give an oil which was dissolved in methanol and this solution was treated with sodium borohydride (2 g) at 0° C. After 2 hours the solution was evaporated, diluted with water and extracted with dichloromethane and the product from the dried (MgSO$_4$) organic extracts was chromatographed on silica gel eluting with 5% methanol in chloroform to yield the title compound as an oil; $^1$H n.m.r. $\tau$(CDCl$_3$) 2.00–2.90 (m, 8H); 5.33 (m,1H); 6.12 (s,3H); 6.92–7.57 (m,7H; 2H exchangeable on D$_2$O wash); 8.16–8.50 (m,2H); 8.91 (d,3H). The product was isolated as the hydrochloride salt m.p. 147.5°–150.5° C., as a 55:45 mixture of diastereoisomers.

EXAMPLE 3

N-(2-(4-Carbomethoxyphenyl)-1,1-dimethylethyl)-2-hydroxy-2-(3-trifluoromethylphenyl) ethanamine The title compound was prepared as in Example 1a from 3-trifluoromethylphenyl glyoxal (2.0 g) and 2-(4- carbomethoxyphenyl)-1,1-dimethyl ethanamine (2.0 g) and crystallised from hexane m.p. 88°-90°. $\tau$(CDCl$_3$) 8.93 (6H,s), 6.8-8.0 (4H,m+2H replaceable by D$_2$O), 6.1 (3H,s), 5.33 (1H,m), 2.8 (2H,d,J=8 Hz), 2.2-2.6 (4H,m), 2.03 (2H,d,J=8 Hz).

EXAMPLE 4

N-(3-(4-Carbomethoxyphenyl)-1,1-dimethylpropyl)-2-hydroxy-2-(3-trifluoromethylphenyl)ethanamine The title compound was prepared as in Example 1a from 3-trifluoromethylphenyl glyoxal (2.0 g) and 3-(4-carbomethoxyphenyl)-1,1-dimethylpropylamine (2.6 g) and isolated as the hydrochloride salt monohydrate m.p. 214°-219°. (methanol-ether). $\tau$(DMSO d$_6$) 8.6 (6H,s), 7.8-8.2 (2H,m), 6.6-7.4 (4H,m), 6.1 (3H,s), 5.8 (3H, broad, replaceable by D$_2$O), 4.8 (1H,m), 2.55 (2H,d,J=8 Hz), 2.1-2.4 (4H,m), 2.07 (2H,d,J=8 Hz), 1.3 (1H, broad, replaceable by D$_2$O), 0.33 (1H, broad, replaceable by D$_2$O).

EXAMPLE 5

N-(2-(4-Carbomethoxyphenyl)ethyl)-2-hydroxy-2-(3-trifluoromethylphenyl) ethanamine The title compound was prepared as in Example 1a from 3-trifluoromethylphenyl glyoxal (3.85 g) and 2-(4-carbomethoxyphenyl) ethanamine (3.4 g), and crystallised from hexane m.p. 75-77.5. $\tau$(CDCl$_3$) 7.66 (2H, broad, replaceable by D$_2$O), 5.9-6.5 (6H, m), 6.15 (3H,s), 5.3 (1H,m), 2.75 (2H,d,J=8 Hz), 2.3-2.6 (4H,m), 2.03 (2H,d,J=8 Hz).

EXAMPLE 6

N-(3-(4-Carbomethoxyphenyl)propyl)-2-hydroxy-2-(3-trifluoromethylphenyl)ethanamine The title compound was prepared as in Example 1a from 3-trifluoromethylphenylglyoxal (1.99 g) and 3-(4-carbomethoxyphenyl) propylamine (1.9 g) and crystallised from hexane m.p. 86°-96°. $\tau$(CDCl$_3$) 7.9-8.35 (2H,m), 7.55 (2H, broad, replaceable by D$_2$O), 7.0-7.5 (6H,m), 6.15 (3H,s), 5.3 (1H,m), 2.85 (2H,d,J=8 Hz), 2.3-2.6 (4H,m), 2.05 (2H,d,J=8 Hz).

EXAMPLE 7

N-(2-(4-Carbomethoxyphenyl)-1-R-1-methylethyl)-2-R-2-hydroxy-2-(3-trifluoromethylphenyl)ethanamine A solution of R-3-trifluoromethylstyrene oxide (2.34 g) in ethanol (20 ml) was added dropwise to a stirred boiling solution of 2-(4-carbomethoxyphenyl)-1-R-1-methylethanamine (2.4 g) in ethanol (50 ml). Following complete addition the solution was heated at reflux for 48 hours, the solvent evaporated and the residue chromatographed on silica gel 60 using 2% methanol in chloroform as eluent. The title compound was obtained as an oil and converted to the hydrochloride salt m.p. 175°-179° (methanol-ether) $(\alpha)_D^{25}$-33.5 (ethanol). $\tau$(DMSO d$_6$) 8.85 (3H,d,J=6 Hz), 6.3-7.2 (5H,m), 6.1 (3H,s), 4.75 (1H,m), 3.5 (1H, broad, replaceable by D$_2$O), 2.6 (2H,d,J=8 Hz), 2.1-2.5 (4H,m), 2.05 (2H,d,J=8 Hz), 0.75 (2H, broad, replaceable by D$_2$O).

EXAMPLE 8

N-(2-(4-Carboxamidophenyl)-1-methylethyl)-2-hydroxy-2-(3-trifluoromethylphenyl) ethanamine The title compound was prepared as in Example 1b from 1-(4-carboxamidophenyl)propan-2-one (2.1 g) and 2-hydroxy-2-(3-trifluoromethyl) ethanamine (2.43 g) and crystallised from ethyl acetate as an 8:92 mixture of diastereoisomers, m.p. 156°-161°. $\tau$(CDCl$_3$) 9.07 (3H,d,J=6 Hz), 6.8-8.0 (5H,m,+2H replaceable by D$_2$O), 6.6 (2H, broad, replaceable by D$_2$O), 5.3 (1H,m), 2.8 (2H,d,J=8 Hz), 2.1-2.5 (4H,m), 2.1 (2H,d,J=8 Hz).

EXAMPLE 9

N-(2-(4-N'-Methylcarboxamidophenyl)-1-methylethyl)-2-hydroxy-2-(3-trifluoromethylphenyl)ethanamine N-(2-(4-Carbomethoxyphenyl)-1-methylethyl)-2-hydroxy-2-(3-trifluoromethylphenyl)ethanamine (2.7 g) was dissolved in ethanolic methylamine solution (15 ml) and heated at 100° C. for 5 hours in an autoclave. After cooling, the solution was evaporated and chromatographed on silica gel 60 using 10% methanol in chloroform as eluent. The title compound was obtained as an oil converted to the hydrochloride salt m.p. 164-169 (methanol-ether) and isolated as a 56:44 mixture of diastereoisomers. $\tau$(DMSO d$_6$) 8.85 (3H,d,J=6 Hz), 7.2 (3H,d,J=5 Hz), 6.3-7.3 (5H,m), 4.75 (1H,m), 3.5 (1H, broad, replaceable by D$_2$O), 2.63 (2H,d,J=8 Hz), 2.1-2.4 (4H,m), 2.15 (2H,d,J=8 Hz), 1.5 (1H, bd, replaceable by D$_2$O) 0.65 (2H, broad, replaceable by D$_2$O).

EXAMPLE 10

N-(2-(4-N',N'-Dimethylcarboxamidophenyl)-1-methylethyl)-2-hydroxy-2-(3-trifluoromethylphenyl)ethanamine The title compound was prepared as in Example 1b from 1-(4-N',N'-dimethylcarboxamidophenyl)propan-2-one (1.4 g) and 2-hydroxy-2-(3-trifluoromethylphenyl)ethanamine (1.4 g). The compound was crystallised as the fumarate monohydrate m.p. 153°-158° (ethyl acetate) and isolated as a 48:52 mixture of diastereoisomers. $\tau$(DMSO d$_6$) 8.85 (3H,d,J=6 Hz), 7.1 (6H,s), 6.3-7.4 (5H,m), 4.88 (1H,m), 3.4 (2H,s), 2.6 (4H,s), 2.1-2.4 (4H,m), 0.3 (6H,broad, replaceable by D$_2$O).

EXAMPLE 11

N-(3-(4-N'-Methylcarboxamidophenyl)-1-methylpropyl)-2-hydroxy-2-(3-trifluoromethylphenyl)ethanamine The title compound was prepared as in Example 9 starting from N-(3-(4-carbomethoxyphenyl)-1-methylpropyl)-2-hydroxy-2-(3-trifluoromethylphenyl)ethanamine (2 g), crystallised as the hydrochloride salt m.p. 114-118 (methanol-ether), and isolated as a 47:53 ratio of diastereoisomers. $\tau$(DMSO d$_6$) 8.67 (3H,d,J=6 Hz), 7.6-8.4 (2H,m), 7.2 (3H,d,J=5 Hz), 6.6-7.2 (5H,m), 4.8 (1H,m), 3.6 (1H, broad, replaceable by D$_2$O), 2.7 (2H,d,J=8 Hz), 2.1-2.5 (4H,m), 2.15 (2H,d,J=8 Hz), 1.6 (1H, bd, replaceable by D$_2$O), 0.85 (2H, broad, replaceable by D$_2$O).

EXAMPLE 12

N-(2-(4-N'-Methylcarboxamidophenyl)-1,1-dimethylethyl)-2-hydroxy-2-(3-trifluoromethylphenyl)ethanamine The title compound was prepared as in Example 9 starting from N-(2-(4-carbomethoxyphenyl)-1,1-dimethylethyl)-2-hydroxy-2-(3-trifluoromethylphenyl)ethanamine (1.4 g) and crystallised from dichloromethane m.p. 139°-142°. $\tau$(DMSO d$_6$) 9.04 (6H,s), 7.1-7.4 (7H,m), 5.5-6.5 (2H, broad, replaceable by D$_2$O), 5.31

(1H,m), 2.78 (2H,d,J=8 Hz), 2.1-2.5 (6H,m), 1.69 (1H, broad, replaceable by D$_2$O).

EXAMPLE 13

N-(3-(4-N'-Methylcarboxamidophenyl)-1,1-dimethylpropyl)-2-hydroxy-2-(3-trifluoromethylphenyl)ethanamine The title compound was prepared as in Example 9 starting from N-(3-(4-carbo methoxyphenyl)-1,1-dimethylpropyl)-2-hydroxy-2-(3-trifluoromethylphenyl)ethanamine (850 mg). The compound was isolated as the fumarate m.p. 160-165 (methanol-ether). τ(DMSO d$_6$) 8.7 (6H,s), 7.9-8.3 (2H,m), 7.24 (3H,d,J=4 Hz), 6.7-7.5 (4H,m), 4.9 (1H,m), 3.4 (1H,s), 2.7 (2H,d,J=8 Hz), 2.0-2.4 (6H,m), 1.0-2.2 (4H, broad, replaceable by D$_2$O).

EXAMPLE 14

N-(2-(4-N'-Methylcarboxamidophenyl)ethyl)-2-hydroxy-2-(3-trifluoromethylphenyl)ethanamine The title compound was prepared as in Example 9 starting from N-(2-(4-carbomethoxyphenyl)ethyl)-2-hydroxy-2-(3-trifluoromethylphenyl)ethanamine (0.9 g) and crystallised from dichloromethane m.p. 136°-140°. τ(DMSO d$_6$) 7.0-7.5 (9H,m), 5.3-6.6 (2H, broad, replaceable by D$_2$O), 5.2 (1H, m), 2.73 (2H,d,J=8 Hz), 2.0-2.5 (6H,m), 1.66 (1H, broad, replaceable by D$_2$O).

EXAMPLE 15

N-(2-(2-Chloro-4-carbomethoxyphenyl)-1-methylethyl)-2-hydroxy-2-(3-trifluoromethylphenyl)ethanamine The title compound was prepared as in Example 1b from 1-(2-chloro-4-carbomethoxyphenyl)propan-2-one (2.32 g) and 2-hydroxy-2-(3-trifluoromethylphenyl)ethanamine (2.1 g). The compound crystallised from hexane m.p. 82°-94° as a 40:60 mixture of diastereoisomers. τ(CDCl$_3$) 8.85 (3H,d,J=6 Hz), 6.8-7.6 (5H,m+2H replaceable by D$_2$O), 6.1 (3H,s), 5.3 (1H,m), 2.7 (1H,d,J=8 Hz), 2.3-2.6 (4H,m), 2.1 (2H,d,J=8 Hz), 1.95 (1H,s).

EXAMPLE 16

N-[2-(4-Carbomethoxy-2-methoxyphenyl)-1-methylethyl]-2-hydroxy-2-(3-trifluoromethylphenyl)ethanamine The title compound was prepared as in Example 1b from 1-(4-carbomethoxy-2-methoxyphenyl)propan-2-one (3.0 g) and 2-hydroxy-2-(3-trifluoromethylphenyl)ethanamine (2.77 g). The compound crystallised from hexane m.p. 88°-100° as a 70:30 mixture of diastereoisomers. τ(CDCl$_3$) 8.8 (3H,d,J=6 Hz), 6.7-7.7 (5H,m,+2H replaceable by D$_2$O), 6.1 (3H,s), 6.0 (3H,s), 5.2 (1H, m), 2.8 (2H,d,J=8 Hz), 2.2-2.6 (6H,m).

EXAMPLE 17

N-[2-(4-Carbomethoxy-3-methylphenyl)-1-methylethyl]-2-hydroxy-2-(3-trifluoromethylphenyl)ethanamine The title compound was prepared as in Example 1b from 1-(4-carbomethoxy-3-methylphenyl)propan-2-one (2.0 g) and 2-hydroxy-2-(3-trifluoromethylphenyl)ethanamine (2.0 g), the compound crystallised from hexane m.p. 88°-92° as a 41:59 mixture of diastereoisomers. τ(CDCl$_3$) 8.9 (3H,d,J=6 Hz), 7.4 (3H,s), 6.8-7.8 (5H,m,=2H, replaceable by D$_2$O), 6.1 (3H,s), 5.3 (1H,m), 2.9 (2H,m), 2.3-2.6 (4H,m), 2.1 (1H,dd,J=8 Hz, J=2 Hz).

EXAMPLE 18

N-[3-(4-N'-Methylcarboxamidophenyl)propyl]-2-hydroxy-2-(3-trifluoromethylphenyl)ethanamine The title compound was prepared as in Example 9 starting from N-[3-(4-carbomethoxyphenyl)propyl]-2-hydroxy-2-(3-trifluoromethylphenyl)ethanamine (0.5 g) as isolated as the fumarate salt m.p. 145°-150° (methanol-ether), τ(DMSO d$_6$) 7.8-8.2 (2H,m), 7.25 (3H,d,J=5 Hz), 6.5-7.4 (6H,m), 4.8 (1H,m), 3.31 (1H,s), 2.6 (2H,d,J=8 Hz), 2.0-2.4 (6H,m), 1.55 (1H, bd, replaceable by D$_2$O), 0.0-3.0 (3H,b,replaceable by D$_2$O).

EXAMPLE 19

(RR,SS)-N-[2-(4-Carbomethoxyphenyl)-1-methylethyl]-2-hydroxy-2-(3-trifluoromethylphenyl)ethanamine hydrochloride The title compound was prepared as in Example 16 from 1-(4-carbomethoxyphenyl)propan-2-one and 2-hydroxy-2-(3-trifluoromethylphenyl)ethanamine and converted into the hydrochloride salt. Crystallisation of the salt from ethyl acetate and then two recrystallisations from ethyl acetate/methanol afforded the separated RR:SS diastereoisomer (96% diastereoisomeric purity by glc) mp 199-205. τ(DMSO d$_6$) 8.9 (3H,d, J=6 Hz), 6.1-7.35 (5H,m), 6.1 (3H,s), 4.62 (1H,m), 3.5 (1H, bd,replaceable by D$_2$O), 2.6 (2H,d,J=8 Hz), 2.2-2.4 (4H,m), 2.1 (2H,d,J=8 Hz), -0.2-1.2 (2H,broad,replaceable by D$_2$O).

DEMONSTRATION OF EFFECTIVENESS OF COMPOUNDS (i) ANTI-OBESITY ACTIVITY

The compounds were administered by oral gavage in water or carboxymethyl-cellulose suspension to genetically obese mice daily for 28 days. At the end of the time the carcass composition was determined. The results obtained were as follows:

| COMPOUND OF | DOSE | g LIPID/MOUSE: | |
|---|---|---|---|
| EXAMPLE NO. | mg/kg po | TREATED | CONTROL |
| 1(a) | 10.5 | 16.3 | 21.3 |
| 5 | 10.2 | 23.76 | 26.58 |
| 6 | 10.6 | 24.26 | 26.58 |

(ii) EFFECT ON ENERGY EXPENDITURE

The effect of the compounds on the energy expenditure of mice was demonstrated by means of the following procedure:

Female CFLP mice each weighing approximately 24 g, were give food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content, following the principles described by J. B. de V. Weir, J. Physiol. (London), 109, 1-9, (1949). The food intake of the mice was measured over this same period of 21 hours. The results are expressed as a percentage of the mean food intake or rate of energy expenditure of the mice dosed with water.

| COMPOUND OF EXAMPLE NO. | DOSE mg/kg po | MEAN ENERGY EXPENDITURE (0.3h) | (0.21h) | MEAN FOOD INTAKE |
|---|---|---|---|---|
| 1 (a) | 21.0 | 130 | 112 | 102 |
| 1 (b) mp 73–88 | 21.0 | 168 | 139 | 82 |
| 1 (b) mp 82–85 | 10.5 | 122 | 108 | 93 |
| 2 | 24.0 | 125 | 108 | 103 |
| 3 | 22.0 | 112 | 102 | 103 |
| 4 | 24.9 | 131 | 106 | 73 |
| 5 | 20.4 | 158 | 121 | 79 |
| 6 | 21.2 | 156 | 115 | 89 |
| 7 | 11.6 | 146 | 127 | 73 |
| 8 | 25.2 | 127 | 98 | 85 |
| 9 | 23.2 | 139 | 109 | 93 |
| 10 | 29.4 | 148 | 102 | 76 |
| 11 | 23.9 | 145 | 113 | 89 |
| 12 | 21.9 | 110 | 107 | 94 |
| 13 | 27.5 | 125 | 102 | 93 |
| 14 | 20.8 | 143 | 100* (0–20h) | 46 |
| 15 | 23.1 | 111 | 94 | 65 |
| 16 | 22.8 | 156 | 125 | 83 |
| 17 | 22.0 | 116 | 109 | 103 |
| 19 | 5.8 | 165 | 118* (0–15h) | 77 |

(iii) CARDIAC ACTIVITY

Rat hearts were perfused by the Langendorff procedure. Hearts were dissected free within 30 seconds of death and reverse perfused via the aorta and coronary vessels with Krebs-Ringer bicarbonate solution (pH 7.4, 37° C.) gassed with 95% oxygen:5% carbon dioxide at a flow rate between 8–12 cm$^3$/minute. Responses were observed after injection of drug dissolved in isotonic saline into the perfusion media. Heart rate and tension were displayed on an Ormed MX2P recorder via a tension transducer and heart ratemeter.

Results are expressed as a percentage of the maximum response due to salbutamol.

| COMPOUND OF EXAMPLE NO. | DOSE ADDED TO PERFUSATE (µg) | HEART TENSION | HEART RATE |
|---|---|---|---|
| 1 (a) | 30 | 0 | 0 |
| 1 (b) mp 73–88 | 30 | 0 | 0 |
| 2 | 30 | <0 | 55.0 |
| 3 | 30 | 0 | 0 |
| 4 | 30 | <0 | <0 |
| 5 | 30 | 0 | 11.7 |
| 6 | 30 | 6 | 0 |
| 7 | 30 | 47 | 11.0 |
| 8 | 30 | 16 | 50.0 |
| 9 | 30 | 14 | 11.0 |
| 10 | 30 | 83 | 36.0 |
| 11 | 30 | 5 | 0 |
| 12 | 30 | 17 | <0 |
| 13 | 30 | <0 | <0 |
| 14 | 30 | 5 | 0 |
| 15 | 30 | 20 | 17.0 |
| 16 | 30 | 3 | 0 |
| 17 | 30 | 11 | 0 |

(iv) HYPOGLYCAEMIC ACTIVITY

Female CFLP mice, weighing approximately 25 g, were fasted for 24 hours prior to the study. The compounds under study were administered orally as an aqueous solution to each of 8 mice. 30 minutes later a blood sample (20 cm$^3$) was obtained from the tail for the analysis of blood glucose. Immediately after taking this blood sample, glucose (1 g/kg body weight) was administered subcutaneously to each mouse. 8 mice were given water as a control. Blood samples were then obtained from each mouse at 30 minute intervals for 120 minutes.

Compounds that produced a significant (P<0.05) reduction of blood glucose, compared with control mice given water, at any time interval, were considered active. The area under the blood glucose curve over the 2 hour period after the administration of the glucose was calculated for each compound and compared with the value for control animals.

| COMPOUND OF EXAMPLE NO. | DOSE mg/kg po | % REDUCTION IN AREA UNDER BLOOD GLUCOSE CURVE |
|---|---|---|
| 1 (b) mp 73–88 | 4.76 | 52.1 |
| 1 (b) mp 82–85 | 1.0 | 10.0 |
| 2 | 21.5 | 23.5 |
| 5 | 0.9 | 35.0 |
| 6 | 4.7 | 41.0 |
| 7 | 1.04 | 36.6 |
| 9 | 5.2 | 44.3 |
| 11 | 5.4 | 43.0 |
| 12 | 4.9 | 10.0 |
| 13 | 6.2 | 10.0 |
| 14 | 4.7 | 41.0 |
| 16 | 1.03 | 37.7 |
| 17 | 4.93 | 32.6 |

(v) ANTI-INFLAMMATORY ACTIVITY

The method used is based on that described by G. Tonelli et al (Endocrinology, 77, 625–634, 1965). An inflammation is induced in the rat ear by the application of 50 µl of a 1% solution of croton oil in tetrahydrofuran, test compounds being dissolved in the irritant vehicle. After 6 hours the inflammation is assessed by killing the animals and weighing the ears. Topical anti-inflammatory activity of a compound is generally considered to be shown when a significant (5% level) reduction in ear weight is seen compared to non-drug treated control.

| COMPOUND OF EXAMPLE NO. | DOSE mg/rat ear | ACTIVITY |
|---|---|---|
| 7 | 0.5 | Active |

TOXICITY

No toxic effects were observed in any of the above tests.

We claim:

1. A compound of formula (II):

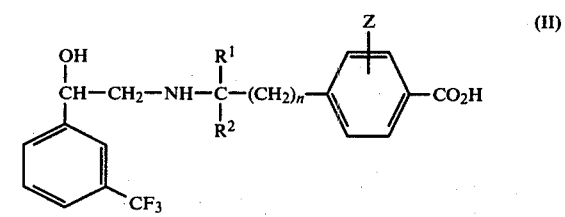

or a pharmaceutically acceptable salt, lower alkyl or aralkyl ester or amide thereof, in which $R^1$ and $R^2$, which may be the same or different, are each hydrogen or methyl, n is 1, 2 or 3, and Z is a $C_{1-6}$ alkyl or $C_{1-6}$ alkoxy or halogen or hydrogen.

2. A compound of formula (III):

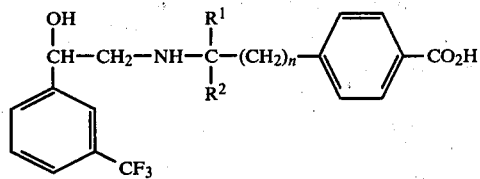

or a pharmaceutically acceptable salt, lower alkyl or aralkyl ester or amide thereof, wherein $R^1$ and $R^2$, which may be the same or different, are each hydrogen or methyl and n is 1, 2 or 3.

3. A compound according to claim 1, in which $R^1$ is hydrogen and $R^2$ is methyl.

4. A compound according to claim 1, in which n is 1.

5. A compound according to claim 1, in which Z is methyl, ethyl, methoxy or ethoxy, or is chlorine or hydrogen.

6. A compound according to claim 1, in which the ester is the methyl, ethyl, propyl or benzyl ester.

7. The compound according to claim 1, which is N-(2-(4-carbomethoxyphenyl)-1-methylethyl)-2-hydroxy-2-(3-trifluoromethylphenyl)ethanamine.

8. A pharmaceutical composition for the treatment of obesity or hyperglycaemia, comprising an effective amount of a compound or a pharmaceutically acceptable salt, ester or amide thereof according to claim 1, together with a pharmaceutically acceptable carrier.

9. A pharmaceutical composition according to claim 8, in unit dosage form.

10. A composition according to claim 9, in which each unit dose contains from 0.1 to 500 mg of said compound of formula (II).

11. A method of treating obesity in human or non-human animals, which comprises administering an effective, non-toxic amount of a compound or a pharmaceutically acceptable salt, ester or amide thereof according to claim 1 to the obese animals.

12. A method of treating hyperglycaemia, in humans, which comprises administering an effective, non-toxic amount of a compound or a pharmaceutically acceptable salt, ester or amide thereof according to claim 1 to hyperglycaemic humans.

* * * * *